United States Patent [19]
Richard

[11] Patent Number: 5,201,716
[45] Date of Patent: Apr. 13, 1993

[54] BLOOD SAMPLE NEEDLE SUPPORT AND EJECTION MECHANISM

[76] Inventor: Lewis G. Richard, 1302 Euclid St., Apt 105, Santa Monica, Calif. 90404

[21] Appl. No.: 901,918

[22] Filed: Jun. 22, 1992

[51] Int. Cl.⁵ ............................................. A61M 5/00
[52] U.S. Cl. ................................... 604/187; 604/243; 128/763
[58] Field of Search .................. 604/187, 240–243; 128/763–765

[56] References Cited

U.S. PATENT DOCUMENTS

| | | | |
|---|---|---|---|
| 2,806,473 | 9/1957 | Lingley | 604/243 |
| 4,822,343 | 4/1989 | Beiser | 604/187 |
| 4,907,600 | 3/1990 | Spencer | 128/764 |
| 4,976,271 | 12/1990 | Blair | 128/764 |
| 5,000,167 | 3/1991 | Sunderland | 128/763 |

*Primary Examiner*—John D. Yasko
*Attorney, Agent, or Firm*—Kelly, Bauersfeld & Lowry

[57] ABSTRACT

A blood specimen collecting system utilizes a disposable needle assembly and standard blood collection and receiving tubes of the type sealed by a pierceable septum. The system includes a hollow cylindrical support adapted to receive a blood collection tube through a rear end thereof and support the needle assembly at a front end thereof. A needle support and ejection mechanism includes a pivotable lever assembly having first and second retainer bracket arms designed to cooperatively engage opposing surfaces of a needle assembly base. The lever assembly is pivotally biased to a first position wherein the first retainer bracket arm applies force to the needle assembly base to bias the needle assembly rearwardly into a small aperture of the cylindrical support. When the lever assembly is manually actuated to overcome the biasing force and is pivoted into a second position, the first retainer bracket arm is disengaged from the forwardly facing portion of the needle assembly base, and then the second retainer bracket arm engages the needle assembly base to apply a forwardly directed ejection force to remove the needle assembly from the hollow cylindrical support.

20 Claims, 1 Drawing Sheet

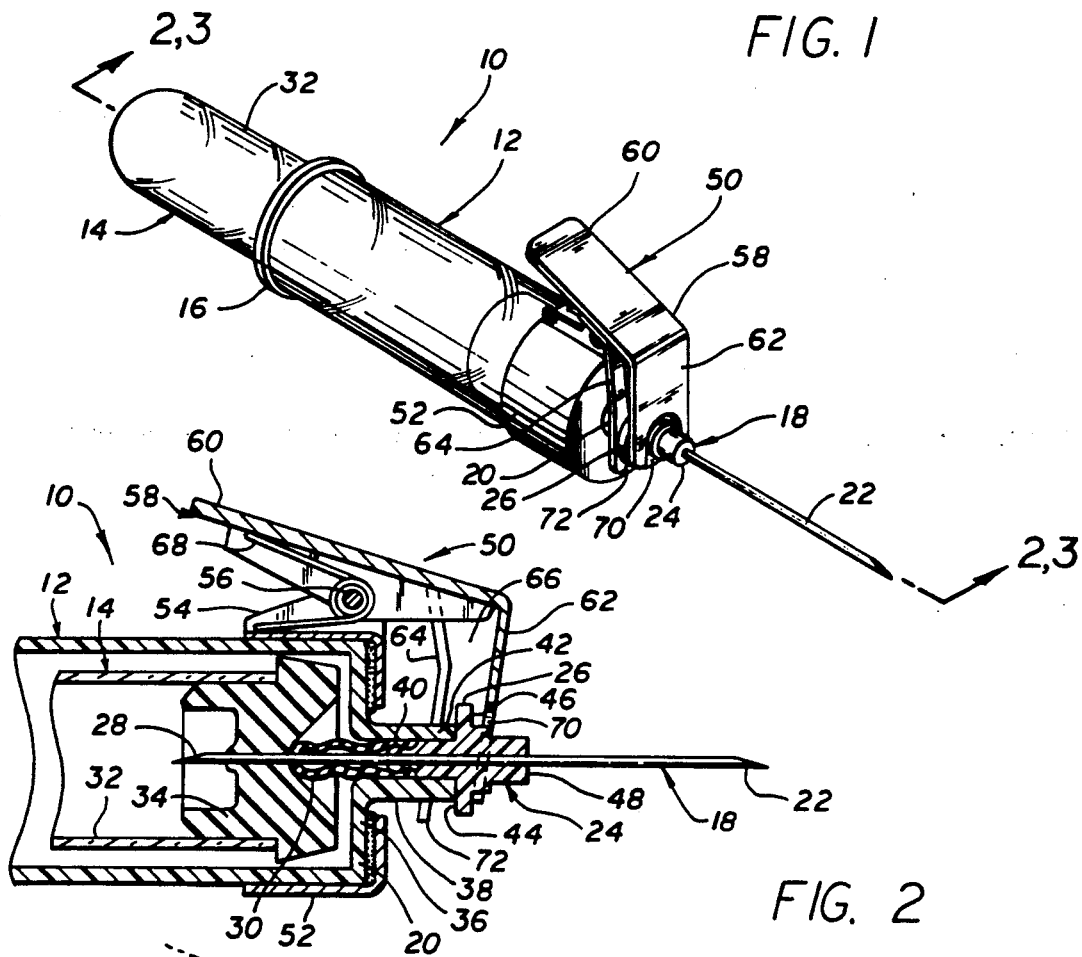
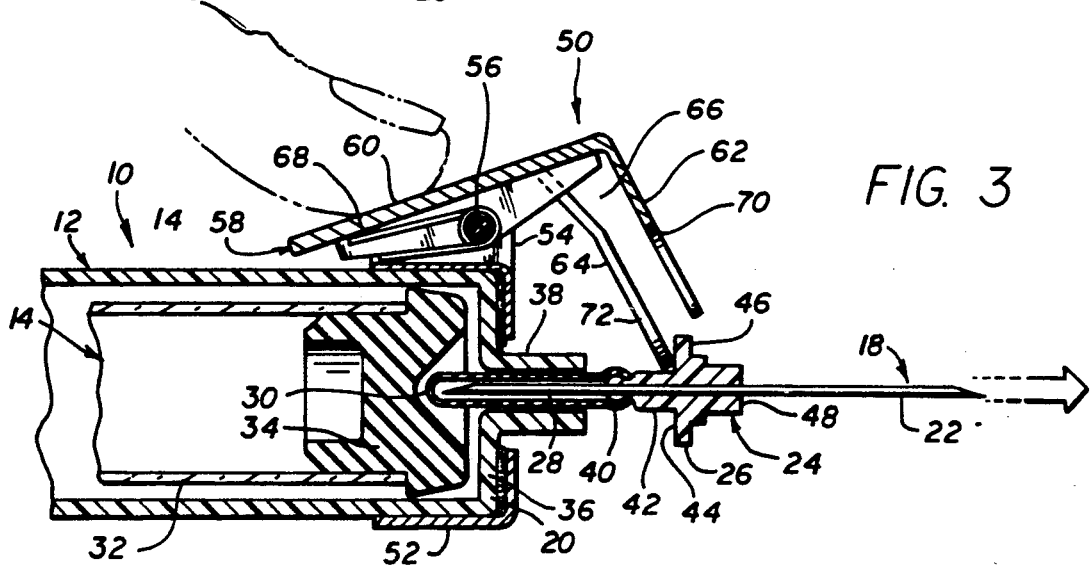

BLOOD SAMPLE NEEDLE SUPPORT AND EJECTION MECHANISM

BACKGROUND OF THE INVENTION

This invention relates generally to blood specimen collection systems. More specifically, the present invention relates to a blood specimen collection system wherein a cylindrical support includes an ejector mechanism which helps to position a needle assembly during use, and conveniently removes and ejects the needle assembly from the cylindrical support for disposal thereof following use.

Many types of blood specimen collecting systems are well known in the art. Currently, hospital and clinical practice require that blood specimens be taken simply, quickly, and with inexpensive and readily disposable equipment. Hypodermic syringes and needles have been satisfactorily used for this purpose for a number of years. It has been found, however, that ordinary hypodermic syringes and needles are less than desirable if blood is to be drawn from a patient for a number of separate tests.

More advanced blood specimen collecting systems have been developed which utilize a disposable needle and apparatus which permit blood to be received into one or more blood collection tubes without requiring that the needle be repeatedly inserted into the patient's vein. The collection tubes which initially receive the blood specimens are utilized to store the blood until the desired blood tests are performed.

Typical state-of-the-art blood specimen collecting systems utilize a standard disposable needle assembly which is placed into a threaded hole in an end wall of a hollow cylindrical support. The standard disposable needle assembly includes an externally extending hollow needle which is transcutaneously inserted into the patient's vein to draw blood, and another needle extending inwardly into the interior of the hollow cylindrical support. The two needles are coaxial and are in fluid communication with one another. Blood collection tubes utilized in such systems are sealed at one end with a breakable elastomeric septum. The collection tube is placed in the interior of the hollow cylindrical support so that the septum is pierced by the inwardly extending needle. The patient's blood is then drawn into the collection tube through the needles without coming into contact with the hollow cylinder.

When the desired amount of blood is received within the collection tube, it is withdrawn from the hollow cylindrical support and the breach through the elastomeric septum through which the inwardly extending needle passed, closes upon itself to seal the collected blood within the tube. Additional blood collection tubes can be inserted into the hollow cylindrical support for collecting additional specimens as described, without withdrawing the externally extending needle from the patient's vein. After the desired blood specimens have been obtained, the needle assembly is withdrawn from the patient and then discarded.

In order to remove the needle assembly from the hollow cylindrical support, it must be grasped and twisted to disengage from the threaded hole. For safety purposes, a protective cap or sheath is typically placed over the externally extending needle prior to attempting to unthread the needle assembly from the cylindrical support. Once the needle assembly is successfully removed from the cylindrical support, it is disposed of, usually by placing the needle assembly into a canister or container specially marked for receiving only such contaminated needles. Since the hollow cylindrical support does not come into contact with the patient's blood, the cylindrical support normally is not discarded after the blood specimen has been collected.

Although such state-of-the-art specimen collecting systems generally work well, they have the inherent disadvantage in that it is necessary to manipulate and touch the needle assembly after the needle has been in contact with the patient's blood. Such manipulation unfortunately gives rise to the possibility of accidently wounding or pricking of a health care worker. This problem arises especially in connection with the step of replacing a protective cap or sheath over the externally extending needle following the collection of blood and prior to disposal of the needle assembly. It is well known in the medical arts that certain serious, even fatal, diseases, such as Hepatitis and AIDS may be spread through accidental contact with infected blood. It is, therefore, imperative that health care workers exercise extreme care when utilizing such prior blood specimen collecting systems to insure that one is not accidentally pricked with a contaminated needle.

Accordingly, there has been a need for an improved blood specimen collecting system wherein exposure to contaminated needles is minimized or eliminated. Such an improved system should preferably permit the collection of blood samples in a manner similar to current state-of-the-art systems, provide for the use of standard blood collection tubes, and require only a minimum level of training of medical personnel to insure proper use thereof. Further, such an improved blood specimen collecting system should be of a simplified design which lends itself to economical manufacturing techniques. The present invention fulfills these needs and provides other related advantages.

SUMMARY OF THE INVENTION

The present invention resides in an improved blood specimen collecting system which permits a double needle assembly to be disposed of after use in a manner minimizing the possibility of inadvertent and unwanted contact with the needle assembly by a medical caregiver. The blood specimen collecting system comprises, generally, a hollow cylindrical support adapted to receive a blood collection tube through a rear end thereof, and which supports a needle assembly at a front end. An ejector mechanism is mounted with respect to the hollow cylindrical support, and includes means for biasing the needle assembly rearwardly into a small front aperture of the cylindrical support when the ejector mechanism is pivoted into a first position. Means are also provided for simultaneously removing a rearwardly biasing force on the needle assembly and applying a forwardly directed ejection force to the needle assembly when the ejector mechanism is pivoted into a second position, to remove the needle assembly from the hollow cylindrical support.

In a preferred form of the invention, the blood collection tube is adapted to fit at least partially within the hollow cylindrical support. The collection tube is sealed at one of its ends by a septum pierceable with a needle. The needle assembly is constructed to include an intermediate base portion which is adapted to be supported within the small aperture provided in the front end of the cylindrical support. A first hollow needle portion extends axially outwardly from the cylindrical support, and a second hollow needle portion extends axially inwardly into the interior of the cylindrical support. The first and second hollow needle portions are in fluid communication with one another. Typically, the first hollow needle portion is adapted to pierce a person's veins, and the second hollow needle portion is adapted to pierce the septum. The needle assembly base includes a rearward portion configured to fit and be mounted in the small aperture provided in the front end of the cylindrical support. An enlarged flange is also provided the needle assembly base, which flange is incapable of fitting within the small aperture. A forwardly extending portion of the base extends opposite the rearward portion relative to the enlarged flange.

The ejector mechanism comprises a lever assembly pivotally mounted relative to the hollow cylindrical support. A base is fixed to a forward end of the hollow cylindrical support, for supporting the lever assembly, and a pivot is fixed relative to the base to provide the means by which the lever assembly is attached to the base. The lever assembly pivots between the first and second positions about the pivot relative to the hollow cylindrical support.

The lever assembly includes spring means for creating the rearwardly directed biasing force which urges the lever assembly toward the first pivotable position. A thumb rest is positioned adjacent to the longitudinally extending exterior surface of the hollow cylindrical support, and provides means for manually actuating the lever assembly. The spring means normally biases the needle assembly rearwardly into the small aperture of the cylindrical support by biasing the ejector mechanism into its first pivotal position. When force is applied to the thumb rest, the biasing force on the needle assembly is overcome, and a forwardly directing ejecting force is applied to the needle assembly as the ejector mechanism is pivoted into the second position. This effectively removes the needle assembly from the hollow cylindrical support.

A first retainer bracket arm extends generally perpendicularly relative to the longitudinal axis of the needle assembly. The first retainer bracket arm engages a forwardly facing portion of the needle assembly base. The first retainer bracket arm is rigidly fixed to the thumb rest and also extends generally perpendicularly therefrom. A first slot is provided in the first retainer bracket arm adjacent to the needle assembly base and is configured to extend at least partially around the forwardly extending portion of the base.

A second retainer bracket arm extends generally perpendicularly to the longitudinal axis of the needle assembly for engaging a rearwardly facing portion of the needle assembly base. Like the first retainer bracket arm, the second retainer bracket arm is rigidly fixed to the thumb rest and extends generally perpendicularly therefrom. The first and second retainer bracket arms are separated from one another by a slot configured to receive the enlarged flange portion of the needle assembly base therein. A second slot is provided in the second retainer bracket arm adjacent to the needle assembly base. The second slot is configured to extend at least partially around the portion of the cylindrical support defining the small aperture without engaging it, and yet engage the enlarged flange of the needle assembly base when the second retainer bracket arm is jointly pivoted into the second position with the first retainer bracket arm.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a blood specimen collecting system embodying the present invention, and specifically showing a needle assembly extending outwardly from a hollow cylindrical support, a blood collection tube inserted within the cylindrical support to engage an inwardly disposed needle, and an ejector mechanism which is fixed relative to the cylindrical support and engages a portion of the needle assembly;

FIG. 2 is an enlarged, fragmented and partially sectional view taken generally along the line 2—2 of FIG. 1; and FIG. 3 is an enlarged, fragmented and partially sectional view similar to that shown in FIG. 2, but illustrating the ejector mechanism pivoted into the second position so as to remove the needle assembly from the hollow cylindrical support.

DETAILED DESCRIPTION OF THE PREFERRED EMBODIMENT

As shown in the drawings for purposes of illustration, the present invention is concerned with an improved blood specimen collecting system, generally designated in FIG. 1 by the reference number 10. The improved blood specimen collecting system 10 comprises a hollow cylindrical support 12 which is adapted to receive a blood collection tube 14 through a rear end 16 thereof, and support a needle assembly 18 at a front end 20 thereof.

The needle assembly 18 includes a first needle 22 which is normally used to penetrate a patient's veins (or other parts of the patient's body) to draw blood. An intermediate base portion of the needle assembly 18 comprises a plastic body 24 of a larger diameter than the first needle 22. The body 24 is substantially cylindrical and includes an enlarged flange 26. A second needle 28 extends from the body 24 in a direction which is opposite to that of the first needle 22. The two needles 22 and 28 are hollow and in fluid communication with one another. Typically, the two needles 22 and 28 comprise the same piece of metal to which the plastic body 24 is attached.

As is standard practice in the art, the needle assembly 18 is usually packaged and stored within protective sheaths (not shown) which are separately removable from the first and second needles 22 and 28. Moreover, the second needle 28 usually carries a protective elastomeric sleeve 30 which may be retracted on the second needle as is shown in FIG. 2.

The blood collection tube 14 comprises a tubular receptacle of glass or plastic 32 and a resilient septum seal 34 capping one end of the tubular receptacle. When the blood collection tube 14 is inserted into the hollow cylindrical support 12, the second needle 28 penetrates the septum seal 34 to extend within the tubular receptacle 32. The interior of the blood collection tube 14 is usually evacuated so as to contain a partial vacuum. Such a vacuum eliminates the need for an air vent or a vented needle during the blood collection process.

The hollow cylindrical support 12 includes a front wall 36 at the front end 20, which forms a sleeve 38. The sleeve 38 defines a small aperture 40 in which a portion of the needle assembly 18 is positioned. More particularly, prior to taking a blood specimen, a portion of the plastic body 24 is fitted into the sleeve 38 to mount the needle assembly 18 to the hollow cylindrical support 12. The blood collection tube 14 is inserted into the hollow cylindrical support 12 through the rear end 16 so that the second needle 28 penetrates the septum seal 34 as sown in FIG. 2. In such a configuration, blood can be drawn from a patient's body into the blood collection tube 14.

After the first needle 22 is withdrawn from the patient's body and the blood collection tube 14 is removed from the cylindrical support 12, the collected blood specimen can be stored in the collection tube 14. The needle assembly 18 which has come into contact with the patient's blood must be discarded. As set forth above, in the past it was often necessary to attempt to replace the protective sheath over the first needle 22 and/or manually manipulate the needle assembly 18 in order to discard it. The present invention facilitates the step of discarding the used needle assembly 18, and thereby render it much less likely that a doctor, nurse or other health care worker should accidentally prick or injure himself with the used needle.

In accordance with the present invention, and as illustrated in FIGS. 1-3, the plastic body 24 forming the intermediate base portion of the needle assembly 18, includes a generally cylindrical rearward portion 42 which is specifically configured to be mounted within the small aperture 40 provided in the front end 20 of the blood collection tube 14. Since the rearward portion 42 is not threaded, it is important that a close friction or interference fit is provided between the rearward portion 42 of the needle assembly base 24, and the interior walls of the sleeve 38. For example, the small aperture 40 will typically have an inner diameter of 0.125 inch. In such a case, the leading end of the rearward portion 42 will typically be constructed to have an outer diameter of 0.1245 inch, which gradually increases to an outer diameter of 0.126 inch. This helps to insure that when the rearward portion 42 is inserted into the small aperture 40, the needle assembly 18 is firmly held in place relative to the hollow cylindrical support 12.

As shown best in FIG. 2, the enlarged flange 26 is sufficiently large to extend beyond the outer diameter of the sleeve 38. As will be discussed hereinafter, a rear face 44 of the enlarged flange 26 is engaged to remove the needle assembly 18 from the hollow cylindrical support 12. A front face 46 of the enlarged flange 26 is engaged to help insure that the rearward portion 42 is securely seated within the small aperture 40 defined by the sleeve 38. The body 24 includes a forward portion 48 having a stepped-cylindrical configuration.

An ejector mechanism 50 is pivotally mounted with respect to the hollow cylindrical support 12. The ejector mechanism 50 provides means for biasing the needle assembly 18, and particularly the base portion 24 thereof, rearwardly into the small aperture 40 defined by the sleeve 38 when the ejector mechanism is pivoted into a first position (FIG. 2). The ejector mechanism 50 also provides means for simultaneously removing a rearwardly biasing force on the needle assembly 18, and applying a forwardly directed ejection force to the rear face 44 of the enlarged flange 26, when the ejector mechanism is pivoted into a second position (FIG. 3).

More specifically, a cap-like base 52 is adhesively secured over the front end 20 of the hollow cylindrical support 12. An aperture is provided in the base 52 through which the sleeve 38 extends. A strut 54 extends outwardly from the base 52 for supporting a pivot rod 56. A lever assembly 58 is mounted to the pivot rod 56, and is capable of moving between the first and second positions mentioned previously.

The lever assembly 58 is a rigid unit that includes a thumb rest 60 which is positioned adjacent to the longitudinally extending surface of the hollow cylindrical support 12. The thumb rest 60 provides means for manually actuating the lever assembly 58. The lever assembly 58 also includes a pair of retainer bracket arms 62 and 64 which are each rigidly fixed to the thumb rest 60 and extend generally perpendicularly therefrom toward the sleeve 38. The first and second retainer bracket arms 62 and 64 are separated from one another by a slot 66 which is configured to receive a portion of the needle assembly base 24 therein, specifically the enlarged flange 26.

A spring 68 is positioned about the pivot rod 56 and is compressed between the under surface of the thumb rest 60 and an outer surface of the base 52. The spring is positioned so as to bias the thumb rest 60, and therefore the entire lever assembly 58, toward the first position (FIG. 2). The particular configuration shown requires a user to depress the thumb rest 60 with sufficient force to overcome the force exerted thereon by the spring 68 in order to move the lever assembly 58 to its second position (FIG. 3).

The first retainer bracket arm 62 extends from the thumb rest 60 generally perpendicularly relative to the longitudinal axis of the needle assembly 18 and the hollow cylindrical support 12. The first retainer bracket arm 62 includes a first slot 70 positioned adjacent to the needle assembly base 24, which is configured to extend at least partially around the forward portion 48 thereof. The portion of the first arm 62 adjacent to the first slot 70 is positioned so as to directly engage the front face 46 of the enlarged flange 26 of the plastic body 24, to bias the needle assembly 18 rearwardly into the small aperture 40 when the lever assembly 58 is pivoted into its first position.

The second retainer bracket arm similarly extends from the thumb rest 60 and is configured to lie generally perpendicularly to the longitudinal axis of the needle assembly 18 and the hollow cylindrical support 12. The second retainer bracket arm 64 includes a second slot 72 provided adjacent to the needle assembly base 24. The second slot 72 is configured to extend at least partially around the sleeve 38 without engaging it, and yet permit the adjacent portion of the second arm 64 to engage the rear face 44 of the enlarged flange 56 when the lever assembly 58 is pivoted into its second position (FIG. 3). It is the force applied to the thumb rest 60 which pivots the lever assembly 58 so that the second retainer bracket arm 64 engages the rear face 44 of the enlarged flange 26, which ejects the needle assembly 18 from the hollow cylindrical support 12.

The use and operation of the blood specimen collecting system 10 of the present invention will now be described. When a blood sample is to be drawn, the skin surrounding the site where the first needle 22 is to be inserted is usually sterilized utilizing an antiseptic solution. A new needle assembly 18 is then mounted to the hollow cylindrical support 12 prior to inserting the first needle 22 into the vein.

Bearing in mind that the first and second needles 22 and 28 are covered by sheaths (not shown), the sheath overlying the second needle 28 is removed to expose the needle and its overlying elastomeric sleeve 30. The sleeve 30 provides a seal over the end of the second needle 28 unless the displaced by the septum seal 34 when the blood collection tube 14 is inserted into the hollow cylindrical support 12. The thumb rest 60 of the lever assembly 58 is depressed to pivot the lever assembly 58 into its second position. The second needle 28 is then inserted through the small aperture 40 defined by the sleeve 38 in the front end 20 of the hollow cylindrical support 12, and the enlarged flange 26 is positioned within the slot 66 defined between the first and second retainer bracket arms 62 and 64. The needle assembly 18, and particularly the plastic body 24, is pushed rearwardly so as to place the rearward portion 42 thereof securely within the sleeve 38. During this procedure the force being applied to the thumb rest 60 is removed so as to permit the first retainer bracket arm 62 to engage the front face 46 of the enlarged flange 26 as shown in FIG. 2.

When so configured, the first needle 22 is inserted into the patient's vein, and then the blood collection tube 14 is inserted into the rear end 16 of the cylindrical support 12 to permit the second needle 28 to pierce the septum seal 34 and place the interior of the tubular receptacle 32 into fluid communication with the patient's blood. When sufficient blood has been collected into the tube 14, it can be removed and a second tube inserted into the cylindrical support 12 in the manner just described to collect additional samples without requiring withdrawal and reinsertion of the first needle 22 into the patient's veins.

When sufficient blood has been collected, the first needle 22 is withdrawn from the patient. The ejector mechanism 50 advantageously permits disposal of the needle assembly 18 without requiring the re-sheathing of the first or second needles 22 and 24, nor any human contact with the needle assembly 18 whatsoever. To remove the needle assembly 18 from the hollow cylindrical support 12, all that is required is that the thumb rest 60 be depressed with sufficient force to overcome the pre-applied counteracting force of the spring 68 to move the lever assembly 58 to its second position (FIG. 3). As the lever assembly 58 is so pivoted, the first retainer bracket arm 62 disengages the front face 46 of the enlarged flange 26, and then the second retainer bracket arm 64 engages the rear face 44 to force the rearward portion 42 of the needle assembly base 24 out of the sleeve 38.

From the foregoing it is to be appreciated that the blood specimen collecting system 10 of the present invention provides apparatus in which a used needle assembly can be discarded without being touched by human hands, thereby minimizing a health care worker's exposure to contaminated needles which may potentially spread dangerous or fatal diseases. Additionally, the collecting system 10 of the present invention is of a simple design lending itself readily to economical manufacturing technics. The system and apparatus of the present invention may be manufactured from medical grade plastics, rubber and stainless steel materials. The system 10 is easy to utilize and is adapted for use with standard blood collection tubes.

Although a particular embodiment of the invention has been described in detail for purposes of illustration, various modifications may be made without departing from the spirit and scope of the invention. Accordingly, the invention is not to be limited, except as by the appended claims.

I claim:

1. A blood specimen collecting system, comprising:
   a hollow cylindrical support adapted to receive a blood collection tube through a rear end thereof and support a needle assembly within a small aperture provided through a front end thereof;
   a blood collection tube adapted to fit at least partially within the hollow cylindrical support, the collection tube being sealed at one of its ends by a septum breakable with a needle;
   a needle assembly having an intermediate base portion adapted to be supported within the small aperture provided in the front end of the cylindrical support, a first hollow needle portion extending axially outwardly from the cylindrical support, and a second hollow needle portion extending axially inwardly into the interior of the cylindrical support, the first and second hollow needle portions being in fluid communication with one another, wherein the first hollow needle portion is adapted to pierce a person's veins, and wherein the second hollow needle portion is adapted to pierce the septum; and
   an ejector mechanism pivotally mounted with respect to the hollow cylindrical support, the ejector mechanism including means for biasing the needle assembly rearwardly into the small aperture of the cylindrical support when the ejector mechanism is pivoted into a first position, and means for simultaneously removing a rearwardly biasing force on the needle assembly and applying a forwardly directed ejection force to the needle assembly when the ejector mechanism is pivoted into a second position, to remove the needle assembly from the hollow cylindrical support.

2. A blood specimen collecting system as set forth in claim 1, wherein the ejector mechanism comprises a lever assembly pivotally mounted relative to the hollow cylindrical support.

3. A blood specimen collecting system as set forth in claim 2, wherein the ejector mechanism includes a base fixed to a forward end of the hollow cylindrical support, for supporting the lever assembly.

4. A blood specimen collecting system as set forth in claim 3, including a pivot fixed relative to the base and to which the lever assembly is attached, about which the lever assembly moves relative to the hollow cylindrical support.

5. A blood specimen collecting system as set forth in claim 2, wherein the ejector mechanism includes a first retainer bracket arm which extends generally perpendicularly relative to the longitudinal axis of the needle assembly, for engaging a forwardly facing portion of the needle assembly base.

6. A blood specimen collecting system as set forth in claim 5, wherein the ejector mechanism includes a second retainer bracket arm which extends generally perpendicularly to the longitudinal axis of the needle assembly, for engaging a rearwardly facing portion of the needle assembly base.

7. A blood specimen collecting system as set forth in claim 6, wherein the lever assembly includes a thumb rest which provides means for manually actuating the lever assembly, the first and second retainer bracket arm are rigidly fixed to the thumb rest and extend generally perpendicularly therefrom, and wherein the first and second retainer bracket arms are separated from one another by a slot configured to receive a portion of the needle assembly base therein.

8. A blood specimen collecting system as set forth in claim 6, wherein the needle assembly base includes a rearward portion configured to fit and be mounted in a small aperture provided in a front end of the cylindrical support, an enlarged flange incapable of fitting within the small aperture, and a forwardly extending portion, wherein the first retainer bracket arm includes a first slot adjacent to the needle assembly base and configured to extend at least partially around the forwardly extending portion of the base and engage a forward face of the enlarged flange, to bias the needle assembly rearwardly into the small aperture of the hollow cylindrical support when the first and second bracket arms are jointly pivoted into the first position.

9. A blood specimen collecting systems as set forth in claim 8, including a second slot provided in the second retainer bracket arm and adjacent to the needle assembly base, wherein the second slot is configured to extend at least partially around the portion of the cylindrical support defining the small aperture without engaging it, and yet engage the enlarged flange of the needle assembly base when the second retainer bracket arm is jointly pivoted into the second position with the first retainer bracket arm, to eject the needle assembly from the hollow cylindrical support.

10. A needle support and ejection mechanism for use in connection with a blood specimen collecting system including a hollow cylindrical support adapted to receive a blood collection tube through a rear end thereof and supporting a needle assembly at a front end thereof, the needle support and ejection mechanism comprising:
a first retainer bracket arm extending generally perpendicularly relative to the longitudinal axis of the needle assembly, for engaging a forwardly facing portion of a needle assembly base;
a second retainer bracket arm extending generally perpendicularly to the longitudinal axis of the needle assembly, for engaging a rearwardly facing portion of the needle assembly base;
means for biasing the first retainer bracket arm into contact with the needle assembly base to apply a rearwardly directed biasing force on the needle assembly; and
means for simultaneously pivoting the first and second retainer bracket arms to remove the rearwardly directed biasing force on the needle assembly and apply a forwardly directed ejection force to the needle assembly to remove the needle assembly from the hollow cylindrical support.

11. A needle support and ejection mechanism as set forth in claim 10, wherein the first and second retainer bracket arms form portions of a lever assembly pivotally mounted relative to the hollow cylindrical support.

12. A needle support and ejection mechanism as set forth in claim 11, wherein the lever assembly includes a thumb rest positioned adjacent to a longitudinally extending exterior surface of the hollow cylindrical support, the thumb rest providing means for manually actuating the lever assembly.

13. A needle support and ejection mechanism as set forth in claim 12, wherein the first and second retainer bracket arms are rigidly fixed to the thumb rest and extend generally perpendicularly therefrom, and wherein the first and second retainer bracket arms are separated from one another by a slot configured to receive a portion of the needle assembly base therein.

14. A needle support and ejection mechanism as set forth in claim 11, wherein the lever assembly includes spring means for creating the rearwardly directed biasing face by biasing the lever assembly toward a first pivotable position, and wherein force applied to the lever assembly pivots the first and second retainer bracket arms into a second pivotable position to remove the needle assembly from the hollow cylindrical support.

15. A needle support and ejection mechanism as set forth in claim 11, including a base fixed to a forward end of the hollow cylindrical support, which base supports the first and second retainer bracket arms.

16. A needle support and ejection mechanism as set forth in claim 15, including a pivot fixed relative to the base and to which the lever assembly is attached, about which the lever assembly moves relative to the hollow cylindrical support.

17. A needle support and ejection mechanism as set forth in claim 10, wherein the needle assembly base includes a rearward portion configured to fit and be mounted in a small aperture provided in the front end of the cylindrical support, an enlarged flange incapable of fitting within the small aperture, and a forwardly extending portion, the needle assembly further including a first hollow needle portion extending axially outwardly from the cylindrical support, and a second hollow needle portion extending axially inwardly into the interior of the cylindrical support, wherein the first and second hollow needle portions are in fluid communication with one another, the first hollow needle portion being adapted to pierce a person's veins, and the second hollow needle portion being adapted to pierce a septum of the blood collection tube.

18. A needle support and ejection mechanism as set forth in claim 17, wherein the first retainer bracket arm includes a first slot adjacent to the needle assembly base and configured to extend at least partially around the forwardly extending portion of the base and engage a forward face of the enlarged flange, to bias the needle assembly rearwardly into the small aperture of the hollow cylindrical support when the first and second bracket arms are jointly pivoted into a first position.

19. A needle support and ejection mechanism as set forth in claim 18, including a second slot provided in the second retainer bracket arm and adjacent to the needle assembly base, wherein the second slot is configured to extend at least partially around the portion of the cylindrical support defining the small aperture without engaging it, and yet engage the enlarged flange of the needle assembly base when the second retainer bracket arm is jointly pivoted into a second position with the first retainer bracket arm, to eject the needle assembly from the hollow cylindrical support.

20. A blood specimen collecting system, comprising:
a hollow cylindrical support adapted to receive a blood collection tube through a rear end thereof and support a needle assembly within a small aperture provided through a front end thereof;
a blood collection tube adapted to fit at least partially within the hollow cylindrical support, the collection tube being sealed at one of its ends by a septum pierceable with a needle;
a needle assembly having an intermediate base portion adapted to be supported within the small aperture provided in the front end of the cylindrical support, a first hollow needle portion extending axially outwardly from the cylindrical support, and a second hollow needle portion extending axially inwardly into the interior of the cylindrical support, wherein the first and second hollow needle portions are in fluid communication with one another, the first hollow needle portion being adapted to pierce a person's veins, and the second hollow needle portion being adapted to pierce the septum, and wherein the needle assembly base includes a rearward portion configured to be mounted in the small aperture provided in the front end of the cylindrical support, an enlarged flange incapable of fitting within the small aperture, and a forwardly extending portion; and an ejector mechanism pivotally mounted with respect to the hollow cylindrical support, the ejector mechanism including means for biasing the needle assembly rearwardly into the small aperture of the cylindrical support when the ejector mechanism is pivoted into a first position, and means for simultaneously removing a rearwardly biasing force on the needle assembly and applying a forwardly directed ejection force to the needle assembly when the ejector mechanism is pivoted into a second position, to remove the needle assembly from the hollow cylindrical support, the ejector mechanism including:

a lever assembly pivotally mounted relative to the hollow cylindrical support;

a base fixed to a forward end of the hollow cylindrical support;

a pivot fixed relative to the base and to which the lever assembly is attached, about which the lever assembly moves relative to the hollow cylindrical support;

spring means for creating the rearwardly directed biasing force;

a thumb rest forming a portion of the lever assembly and positioned adjacent to a longitudinally extending exterior surface of the hollow cylindrical support, wherein the thumb rest provides means for manually actuating the lever assembly;

a first retainer bracket arm for engaging a forward face of the enlarged flange, the first retainer bracket arm being rigidly fixed to the thumb rest and including a first slot adjacent to the needle assembly base which is configured to extend at least partially around the forwardly extending portion and engage the forward face of the enlarged flange; and a second retainer bracket arm for engaging a rear face of the needle assembly base enlarged flange, wherein the second retainer bracket arm is rigidly fixed to the thumb rest and is separated from the first arm by a slot configured to receive the needle assembly base enlarged flange therein, the second retainer bracket arm including a second slot adjacent to the needle assembly base which is configured to extend at least partially around a portion of the cylindrical support defining the small aperture without substantially engaging it, and yet engage enlarged flange at the needle assembly base when the second retainer bracket arm is jointly pivoted into the second position with the first retainer bracket arm, to eject the needle assembly from the hollow cylindrical support.

* * * * *